(12) United States Patent
Wada et al.

(10) Patent No.: US 8,524,876 B2
(45) Date of Patent: Sep. 3, 2013

(54) RNAI MOLECULE TARGETING THYMIDYLATE SYNTHASE AND APPLICATION THEREOF

(75) Inventors: Hiromi Wada, Shiga (JP); Cheng Long Huang, Kyoto (JP)

(73) Assignee: Delta-Fly Pharma, Inc., Tokushima-Shi (JP)

( * ) Notice: Subject to any disclaimer, the term of this patent is extended or adjusted under 35 U.S.C. 154(b) by 49 days.

(21) Appl. No.: 13/258,591

(22) PCT Filed: Mar. 29, 2010

(86) PCT No.: PCT/JP2010/055521
§ 371 (c)(1),
(2), (4) Date: Sep. 22, 2011

(87) PCT Pub. No.: WO2010/113844
PCT Pub. Date: Oct. 7, 2010

(65) Prior Publication Data
US 2012/0016012 A1    Jan. 19, 2012

(30) Foreign Application Priority Data
Mar. 31, 2009    (JP) ................................. 2009-086463

(51) Int. Cl.
*C07H 21/04*    (2006.01)
(52) U.S. Cl.
USPC ........................................................ 536/24.1
(58) Field of Classification Search
USPC ........................................................ 536/24.5
See application file for complete search history.

(56) References Cited

U.S. PATENT DOCUMENTS

2005/0246794 A1 * 11/2005 Khvorova et al. ............ 800/286
2009/0318453 A1    12/2009 Okabe

FOREIGN PATENT DOCUMENTS

| JP | 2005-253342 A | 9/2005 |
| WO | WO 2008/035481 A1 | 3/2008 |
| WO | WO 2008/124927 A1 | 10/2008 |

OTHER PUBLICATIONS

Huang et al., "E2F1 Overexpression Correlates with thymidylate Synthase and Survivin Gene Expressions and Tumor Proliferation in Non-Small-Cell Lung Cancer", Clinical Cancer Research, Dec. 1, 2007, vol. 13, No. 23, pp. 6938-6946.
International Search Report, PCT/JP2010/055521, May 25, 2010.
Kadota et al., "Combined therapy with TS-suppressing adenoviral vector and 5-FU against 5-FU resistant cancer cell", Dai 67 Kai The Japanese Cancer Association Koen Yoshishu, 2008, pp. 235-236.
Kawakami., "Takei Idenshi Hyotekigata RNA Kansho ni yoru Gan Order Made Chiryo Kaihatsu", Kanazawa University Cancer Research Institute Bunshi Hyoteki Yakuzai Kaihatsu Center 2005-nendo Hokokusho (special Edition), 2005, pp. 74-76.
Takeishi et al., "Nucleotide sequence of a functional cDNA for human thymidylate synthase", Nucleic Acids Research, Mar. 25, 1985, vol. 13, No. 6, pp. 2035-2043.
First Office Action issued Jul. 9, 2012, in Chinese Patent Application No. 201080015581.6, with English translation.
Mishima et al., "Novel double-stranded RNA as interfering RNA for suppressing expression of thymidylic acid synthetase enzyme within cell, useful in preparation of composition for treating cell proliferative disease such as cancer," DWPI Derwent World Patent Library, DW 200564, pp. 1-2, Oct. 6, 2005.
Extended European Search Report issued Oct. 31, 2012, in European Patent Application No. 10758615.8.
Ferguson et al., "Antisense down-reguiation of thymildylate synthase to suppress growth and enhance cytotoxicity of 5-FUdR, 5-FU and Tomudex in HeLa cells," British Journal of Pharmacology (1999), vol. 127, pp. 1777-1786.
Ju et al., "Desensitization and Sensitization of Cells to Fluoropyrimidines with Different Antisenses Directed against Thymidylate Synthase Messenger RNA," Clinical Cancer Research (Sept. 1998), vol. 4, pp. 2229-2236.
Schmitz et al., "Small interfering Double-Stranded RNAs as Therapeutic Molecules to Restore Chemosensitivity to Thymidylate Synthase Inhibitor Compounds," Cancer Research (Feb. 15, 2004), vol. 64, pp. 1431-1435.

* cited by examiner

*Primary Examiner* — Brian Whiteman
(74) *Attorney, Agent, or Firm* — Birch, Stewart, Kolasch & Birch, LLP

(57) ABSTRACT

This invention provides a novel RNAi molecule that can significantly potentiate antitumor effects of a 5-FU antitumor agent. The RNAi molecule comprises the nucleotide sequence shown in SEQ ID NO: 2. The invention also provides an antitumor agent comprising such RNAi molecule and a 5-FU antitumor agent.

15 Claims, 2 Drawing Sheets

RNAI MOLECULE TARGETING THYMIDYLATE SYNTHASE AND APPLICATION THEREOF

TECHNICAL FIELD

The present invention relates to an RNAi molecule targeting thymidylate synthase, an antitumor agent containing the RNAi molecule, an agent for potentiating antitumor effects of a 5-FU antitumor agent containing the RNAi molecule, and a pharmaceutical composition containing the RNAi molecule and the 5-FU antitumor agent (a combination drug comprising tegafur, gimeracil, and oteracil potassium, in particular).

BACKGROUND ART

5-FU antitumor agents, such as 5-fluorouracil (hereafter, referred to as "5-FU"), a combination drug comprising tegafur and uracil, or a combination drug comprising tegafur, gimeracil, and oteracil potassium (a compound drug containing tegafur, gimeracil, and oteracil potassium at a ratio of 1:0.4:1 by mole, hereafter referred to as "S-1"), are generally used in treatment of various types of cancer, including digestive system cancer and non-small-cell lung cancer. Thymidylate synthase (hereafter, referred to as "TS") involved in DNA synthesis is known as a target molecule of 5-FU. The correlation between the TS expression level and sensitivity to 5-FU antitumor agents has heretofore been reported as a result of many clinical trials. Specifically, the effects of 5-FU antitumor agents are remarkable for cancer patients exhibiting relatively low TS expression levels, although many cancer patients exhibing relatively high TS expression levels have resistance to 5-FU antitumor agents (Patrick G. Johnston et al., Cancer Res., 1995; 55: 1407-12; Kun-Huei Yeh et al., Cancer, 1998; 82: 1626-31). Accordingly, development of a novel cancer treatment technique for potentiating the antitumor effects of 5-FU antitumor agents is awaited for cancer patients exhibiting high TS expression levels and having resistance to 5-FU antitumor agents.

It was also reported that TS expression could be suppressed with the utilization of RNA interference (hereafter, referred to as "RNAi"), which had been developed as a tool for suppressing the expression of a given gene (JP Patent Publication (Kokai) No. 2005-253342 A). Accordingly, attempts to potentiate antitumor effects of 5-FU antitumor agents have been made through suppression of TS expression via RNAi, although the effects of potentiating antitumor effects are not yet satisfactory (Kadota et al., the 67th Annual Meeting of the Japanese Cancer Association, 2008, p. 235, P-4274).

SUMMARY OF THE INVENTION

Object to Be Attained By the Invention

The present invention is intended to provide a novel RNAi molecule that can remarkably potentiate antitumor effects of 5-FU antitumor agents.

Means for Attaining the Object

Under the above circumstances, the present inventors have conducted studies regarding a novel RNAi molecule that can remarkably potentiate antitumor effects of 5-FU antitumor agents. As a result, they discovered a novel RNAi molecule that can suppress TS expression at a particularly remarkable level. Also, the present inventors confirmed that such RNAi molecule would remarkably suppress TS expression and consequently exert antitumor effects and potentiate the antitumor effects of 5-FU antitumor agents (a combination drug comprising tegafur, gimeracil, and oteracil potassium, in particular). This has led to the completion of the present invention.

Specifically, the present invention is as described below.

[1] An RNAi molecule capable of suppressing expression of thymidylate synthase by RNAi action comprising a double-stranded RNA domain composed of a sense strand consisting of the nucleotide sequence represented by SEQ ID NO: 1, 3, or 5 hybridized to an antisense strand hybridizing under stringent conditions to the sense strand.

[2] The RNAi molecule according to [1], which comprises any of the following combinations of a sense strand and an antisense strand:

a sense strand consisting of the nucleotide sequence represented by SEQ ID NO: 1 and an antisense strand consisting of the nucleotide sequence represented by SEQ ID NO: 2;

a sense strand consisting of the nucleotide sequence represented by SEQ ID NO: 3 and an antisense strand consisting of the nucleotide sequence represented by SEQ ID NO: 4; or a sense strand consisting of the nucleotide sequence represented by SEQ ID NO: 5 and an antisense strand consisting of the nucleotide sequence represented by SEQ ID NO: 6.

[3] The RNAi molecule according to [1] or [2], wherein the sense strand is ligated to the antisense strand via a linker region.

[4] The RNAi molecule according to [3], which consists of the nucleotide sequence represented by SEQ ID NO: 8.

[5] A vector comprising template DNA of the RNAi molecule according to [3] or [4] and expressing the RNAi molecule.

[6] An antitumor agent comprising the RNAi molecule according to any of [1] to [4] and/or the vector according to [5].

[7] A pharmaceutical composition used for treatment and/or prevention of cancer comprising the RNAi molecule according to any of [1] to [4] and/or the vector according to [5] in combination with a 5-FU antitumor agent.

[8] The pharmaceutical composition according to [7], wherein the 5-FU antitumor agent is a combination drug comprising tegafur.

[9] The pharmaceutical composition according to [8], wherein the 5-FU antitumor agent is a combination drug comprising tegafur, gimeracil, and oteracil potassium.

[10] The pharmaceutical composition according to [9], which comprises tegafur, gimeracil, and oteracil potassium at a ratio of 1:0.4:1 by mole.

[11] The pharmaceutical composition according to any of [7] to [10], wherein the RNAi molecule according to any of [1] to [4] and/or the vector according to [5], and the 5-FU antitumor agent are each a single-active-ingredient preparation.

[12] The pharmaceutical composition according to any of [7] to [10], wherein the RNAi molecule according to any of [1] to [4] and/or the vector according to [5] and the 5-FU antitumor agent are in the form of a kit formulation.

[13] An agent for potentiating antitumor effects of a 5-FU antitumor agent comprising the RNAi molecule according to any of [1] to [4] and/or the vector according to [5].

[14] The agent for potentiating antitumor effects according to [13], wherein the 5-FU antitumor agent is a combination drug comprising tegafur.

[15] The agent for potentiating antitumor effects according to [14], wherein the 5-FU antitumor agent is a combination drug comprising tegafur, gimeracil, and oteracil potassium.

This description includes part or all of the contents as disclosed in the description and/or drawings of Japanese Patent Application No. 2009-086463, which is a priority document of the present application.

EFFECTS OF THE INVENTION

The RNAi molecule of the present invention is capable of suppressing TS expression at a particularly remarkable level and is capable of suppressing the growth of tumors expressing TS. Further, the RNAi molecule of the present invention is capable of potentiating antitumor effects of the 5-FU antitumor agent (a combination drug comprising tegafur, gimeracil, and oteracil potassium, in particular) at a remarkable level.

EMBODIMENTS OF THE INVENTION

Figure 1:
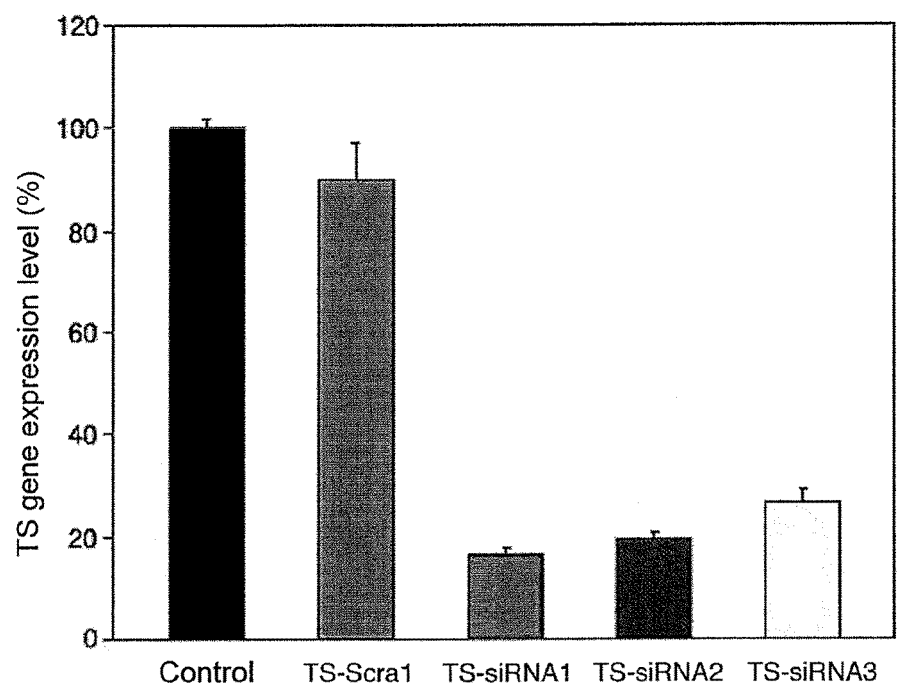
FIG. 1 is a characteristic diagram showing effects of TS-targeted siRNA for suppressing TS expression in DLD-1/5FU human colorectal cancer cell lines.

The RNAi molecule of the present invention comprises a double-stranded RNA domain composed of a sense strand consisting of the nucleotide sequence represented by SEQ ID NO: 1, 3, or 5 hybridized to an antisense strand having a nucleotide sequence complementary to the nucleotide sequence of the sense strand. The RNAi molecule of the present invention targets an mRNA domain of TS having a nucleotide sequence identical to that of the sense strand (hereafter, referred to as the "target mRNA domain"). It thus exhibits RNAi actions in a TS-specific manner, and it can remarkably suppress TS expression.

The situation in which the RNAi molecule of the present invention "targets" the target mRNA domain takes place under conditions in which an antisense strand of a double-stranded RNA domain of the RNAi molecule of the present invention is capable of hybridizing to the target mRNA domain under stringent conditions.

Stringent conditions can be determined based on the melting temperature (Tm) of a nucleic acid hybridizing in accordance with a conventional technique. Under stringent conditions in which the hybridized state can be maintained, for example, washing is generally carried out in approximately 1×SSC, 0.1% SDS at 37° C. Under more stringent conditions, washing is carried out in approximately 0.5×SSC, 0.1% SDS at 42° C. Under still more stringent conditions, washing is carried out in approximately 0.1×SSC, 0.1% SDS at 65° C.

An antisense strand in a double-stranded RNA domain of the RNAi molecule of the present invention is preferably RNA consisting of a nucleotide sequence completely complementary to the target mRNA domain. As long as hybridization can be carried out under stringent conditions, an antisense strand may comprise a mismatch, including a deletion, a substitution, or an addition, of 1 to 3 nucleotides, preferably 1 or 2 nucleotides, and more preferably 1 nucleotide.

Preferably, the RNAi molecule of the present invention comprises a double-stranded RNA domain comprising a sense strand hybridized to an antisense strand as described below:

a sense strand consisting of the nucleotide sequence represented by SEQ ID NO: 1 and an antisense strand consisting of the nucleotide sequence represented by SEQ ID NO: 2;

a sense strand consisting of the nucleotide sequence represented by SEQ ID NO: 3 and an antisense strand consisting of the nucleotide sequence represented by SEQ ID NO: 4; or a sense strand consisting of the nucleotide sequence represented by SEQ ID NO: 5 and an antisense strand consisting of the nucleotide sequence represented by SEQ ID NO: 6.

Particularly preferably, the RNAi molecule of the present invention comprises a double-stranded RNA domain composed of a sense strand consisting of the nucleotide sequence represented by SEQ ID NO: 1 hybridized to an antisense strand consisting of the nucleotide sequence represented by SEQ ID NO: 2.

A sense or antisense strand constituting the RNAi molecule of the present invention may comprise an overhang at the 3' end, according to need. Types and numbers of nucleotides constituting such overhang are not limited. For example, an overhang sequence may consist of 1 to 5, preferably 1 to 3, and more preferably 1 or 2 nucleotides (e.g., TTT, UU, or TT). In the present invention, an "overhang" is a nucleotide added to the end of a strand constituting an RNAi molecule having no nucleotide at a corresponding position of the other strand to which such "overhang" can complementarily bind. An overhang may be a nucleotide constituting DNA. In addition, a sense or antisense strand constituting the RNAi molecule may further include a substitution, an addition, or a deletion of 1 to 3 nucleotides, and more preferably 1 or 2 nucleotides, according to need, provided that RNAi activity is not influenced, so that a variety of experimental operations, such as gene sequencing, can be smoothly performed.

Also, the 5' end of a sense or antisense strand may be phosphorylated, or triphosphoric acid (ppp) may be bound to the 5' end, according to need.

Examples of the RNAi molecules of the present invention include double-stranded RNA molecules, such as siRNA (small interfering RNA) molecules and shRNA (short hairpin RNA) molecules, and siRNA and shRNA molecules are preferable.

In the present invention, an siRNA molecule is a double-stranded RNA molecule resulting from formation of a double-stranded region via hybridization of a sense strand to an antisense strand.

A sense strand and an antisense strand constituting an siRNA molecule can be synthesized in vitro in accordance with a known technique, such as chemical synthesis or utilization of a transcription system using a promoter and an RNA polymerase. Alternatively, template DNAs of the sense strand and the antisense strand may be introduced into an adequate expression vector, and the resulting vector may be administered into an adequate host cell to synthesize the sense and antisense strands of interest in vivo. The synthesized sense and antisense strands can be subjected to annealing via a common method known in the art. The synthesized sense and antisense strands are separately dissolved in an annealing buffer for double-stranded RNA, equivalent amounts (equal number of moles) thereof are mixed with each other, the mixture is heated until the double strand is dissociated, and the resultant is then incubated with gradual cooling. Annealing can be carried out by allowing the mixture to stand at 90° C. for 1 minute and then at 37° C. for 1 hour, for example. Thereafter, phenol/chloroform extraction and ethanol precipitation are carried out, and an siRNA molecule (i.e., a double-stranded RNA molecule) can be obtained.

In the present invention, an shRNA molecule is single-stranded RNA consisting of the sense strand ligated to the antisense strand via a linker region. It consists of 40 to 60 nucleotides, the linker region is folded via loop formation, and the antisense strand is hybridized to the sense strand. Thus, a double-stranded region is formed.

A linker region contained in an shRNA molecule is not particularly limited, and it may be a polynucleotide or non-polynucleotide linker, provided that it is capable of ligating the sense strand to the antisense strand to form a stem-loop structure. A polynucleotide linker consisting of 2 to 22 nucleotides known in the art is preferable. Specific examples include UAGUGCUCCUGGUUG (SEQ ID NO: 7), UUCAAGAGA, CCACC, CUCGAG, CCACACC, UUCAAGAGA, AUG, CCC, and UUCG, with UAGUGCUCCUGGUUG (SEQ ID NO: 7) being preferable.

A preferable shRNA molecule is single-stranded RNA consisting of the nucleotide sequence represented by SEQ ID NO: 8.

An shRNA molecule can be synthesized in vitro or in vivo in accordance with known techniques as described above. When synthesizing an shRNA molecule, a single RNA strand comprising a sense strand and an antisense strand oriented in opposite directions is synthesized, and the resulting single RNA strand is then subjected to self-complementary binding to form a double-strand strucutre. Thus, an shRNA molecule can be obtained.

Also, an shRNA molecule can be obtained with the use of an expression vector comprising template DNA encoding the shRNA molecule.

Examples of vectors that can be used in the present invention include plasmid, viral, and non-viral vectors. Examples of plasmid vectors that can be used include pBAsi, pSUPER, and pBAsi-hU6 vectors. Examples of viral vectors that can be used include adenovirus (e.g., pAxcwit), retrovirus, and lentivirus vectors. An example of a non-viral vector is a liposome vector.

A promoter and/or another control sequence is operably linked to template DNA of an shRNA molecule and the resultant is inserted into a vector. The expression "operably linked . . . inserted" refers to the ligation and incorporation of a promoter and/or another control sequence into the vector, so that the shRNA molecule is expressed and mRNA of target TS is degraded under the control of a promoter and/or another control sequence in a cell into which such vector has been introduced. The promoter and/or other control sequence that can be incorporated into a vector are not particularly limited. A promoter and/or other control sequence known in the art, such as a constitutive promoter, tissue-specific promoter, stage-specific promoter, tRNA promoter, H1 promoter, U6 promoter, polymerase II promoter, CMV promoter, and another control element (e.g., a terminator sequence comprising at least 4 continuous thymidine residues), can be adequately selected.

The thus-prepared vector expressing an shRNA molecule is capable of expressing an shRNA molecule and specifically degrading TS mRNA in a cell into which the vector has been introduced.

The RNAi molecule of the present invention may be administered by any method, provided that it is capable of exerting its effects in the tumor. The RNAi molecule can be administered into the tumor or blood. When the RNAi molecule of the present invention is administered into the blood, the RNAi molecule may be modified by a known nucleic acid modification technique, so as to prevent the RNAi molecule from degrading. In addition, known drug delivery systems (DDSs), such as liposomes or polymeric micells, can be employed, so that the RNAi molecule can easily reach the tumor.

The shRNA-molecule-expressing vector of the present invention can be introduced into a cell via, for example, carrier-mediated transport mediated by a lipid (e.g., the lipofectamine method), transport mediated by a chemical substance (e.g., calcium phosphate), microinjection, implantation with a gene gun, or electroporation.

Effects of the RNAi-molecule or the shRNA-molecule-expressing vector of the present invention can be evaluated by using, as an indicator, the lowered expression levels of mRNA or proteins of TS in cells, tissue, or an individual into which such molecule or vector has been introduced, compared with those in cells, tissue, or an individual into which such molecule or vector has not been introduced (or has not yet been introduced). When mRNA is to be assayed, mRNA can be assayed via Northern hybridization, RT-PCR, in situ hybridization, or other means. When proteins are to be assayed, proteins can be assayed via Western blotting, ELISA, protein assay with the use of a protein chip to which an antibody has been bound, or protein activity assay or by other means.

The RNAi-molecule or the shRNA-molecule-expressing vector of the present invention is capable of lowering the mRNA or protein expression levels of TS in cells, tissue, or an individual into which such molecule or vector has been introduced by 50% or higher, 60% or higher, 70% or higher, preferably 80% or higher, and more preferably 90% or higher, compared with a control sample.

The RNAi-molecule or the shRNA-molecule-expressing vector of the present invention is capable of exerting effects of suppressing TS expression at two, three, four, five, ten, twenty, thirty, forty, fifty, one hundred, or more times the efficacy of RNAi-molecule or the shRNA-molecule-expressing vectors known in the art that target TS mRNA.

A variety of techniques are known as methods for selecting nucleotide sequences in the target mRNA domain for the design of RNAi molecules. For example, the siRNA Design Support System (Takara Bio, Inc.) can be employed. However, it should be noted that not all RNAi molecules having nucleotide sequences selected via such technique have RNAi actions. Thus, it is very difficult to select RNAi molecules of interest having effects of significantly suppressing TS expression from among the candidate RNAi molecules having nucleotide sequences selected via the aforementioned technique.

The RNAi-molecule or the shRNA-molecule-expressing vector described above can be used as an active ingredient of (a) an antitumor agent, (b) an agent for potentiating antitumor effects of a 5-FU antitumor agent, and (c) a pharmaceutical composition used for treatment and/or prevention of cancer.

(a) Antitumor Agent

As described in detail in the examples below, the RNAi-molecule or the shRNA-molecule-expressing vector of the present invention is capable of suppressing tumor cell growth. Thus, the RNAi-molecule or the shRNA-molecule-expressing vector of the present invention can be used as an antitumor agent for treatment and/or prevention of cancer.

Cancers exhibiting high TS expression levels can be treated with the use of the antitumor agent of the present invention. Examples of such cancers include, but are not particularly limited to, colorectal cancer, liver cancer, kidney cancer, head and neck cancer, esophageal cancer, gastric cancer, biliary tract cancer, gallbladder and bile duct cancer, pancreatic cancer, lung cancer, breast cancer, ovarian cancer, cervical cancer, uterine body cancer, bladder cancer, prostate cancer, testicular tumor, osteogenic and soft-tissue sarcomas, leukaemia, malignant lymphoma, multiple myeloma, skin cancer, and brain tumor. Preferable examples are colorectal cancer, gastric cancer, head and neck cancer, lung cancer, breast cancer, pancreatic cancer, biliary tract cancer, and liver cancer, with colorectal cancer being particularly preferable.

The antitumor agent of the present invention may comprise the RNAi-molecule or the shRNA-molecule-expressing vector of the present invention alone or in combinations of two or more. Use of the shRNA-molecule-expressing vector as an active ingredient of the antitumor agent of the present invention is preferable for the following reasons. That is, use of such vector is more cost effective than synthesis of RNAi molecules, such vector is amplified after introduction into cells, and, shRNA molecules can be mass-produced with stability. Thus, use of such vector is quantitatively more efficient than introduction of RNAi molecules. The shRNA expression vector preferably expresses the shRNA molecule represented by SEQ ID NO: 8.

The antitumor agent of the present invention may comprise, in addition to the RNAi-molecule or the shRNA-molecule-expressing vector of the present invention, adequate substances that are generally used, such as carriers, diluents, emulsions, excipients, fillers, binders, wetting-out agents, disintegrators, surface active agents, lubricants, dispersants, buffers, preservatives, solubilizers, antiseptics, colorants, flavoring agents, or stabilizers.

The antitumor agent of the present invention can be directly administered for cancer via injection. It can also be administered through an oral or parenteral route (e.g., intravenous administration, intraarterial administration, topical administration via injection, intraperitoneal or intrathoracic administration, subcutaneous administration, intramuscular administration, sublingual administration, percutaneous absorption, or intrarectal administration).

The antitumor agent of the present invention can be prepared in an adequate dosage form in accordance with the route of administration. Specifically, the antitumor agent can be prepared in various dosage forms, such as injection preparations, suspensions, emulsifiers, ointments, creams, tablets, capsules, granule preparations, powder preparations, pills, fine grains, troches, drug preparations for intrarectal administration, oleagenous suppositories, or water-soluble suppositories.

The amount of the RNAi-molecule or the shRNA-molecule-expressing vector of the present invention to be incorporated into the antitumor agent of the present invention can vary depending on factors such as age, body weight, or severity of a patient's disease. A dose can be adequately determined within the range from 0.0001 mg to 100 mg per kg of body weight.

The RNAi-molecule or the shRNA-molecule-expressing vector contained in the antitumor agent of the present invention can be delivered to the target tissue or cells via a variety of techniques that are commonly employed in the field of gene therapy. For example, known DDS techniques such as those using liposomes or polymeric micells, carrier-mediated transport mediated by a lipid (e.g., the lipofectamine method), transport mediated by a chemical substance (e.g., calcium phosphate), microinjection, implantation with a gene gun, or electroporation can be employed, as described above.

Effects of the antitumor agent of the present invention can be evaluated by administering the antitumor agent to cells or tissue originating from cancer or to individuals afflicted with cancer, comparing the tumor size thereof with that of cells, tissue, or an individual to which the antitumor agent has not been administered (or not yet been administered), and using the results of comparison (i.e., tumor shrinkage or elimination) as an indicator. Cancer cells that can be used for evaluation of the effects of the antitumor agent of the present invention are not particularly limited, provided that TS is expressed. Examples thereof include the DLD-1/5FU, KM12C/5FU, and HT29/5FU human colorectal cancer cell lines and the NUGC-3/5FU human gastric cancer cell line.

The antitumor agent of the present invention is capable of exerting antitumor effects that are two, three, four, five, ten, twenty, thirty, forty, fifty, one hundred, or more times as great as an antitumor agent comprising, as an active ingredient, RNAi-molecule or shRNA-molecule-expressing vectors that target TS mRNA known in the art.

(b) Agent for Potentiating Antitumor Effects of 5-FU Antitumor Agent

It is well-known in the art that tumors exhibiting high TS expression levels can be resistant to the 5-FU antitumor agent (Johnston P. G. et al., Cancer Res., 1995; 55: 1407-12; Yeh K. H. et al., Cancer, 1998; 82: 1626-31). As specifically described in the examples below, the agent for potentiating antitumor effects of the 5-FU antitumor agent according to the present invention is capable of suppressing TS expression in such tumors and potentiating the effects of a 5-FU antitumor agent administered.

In the present invention, examples of 5-FU antitumor agents include 5-FU and a 5-FU derivative comprising 5-FU as an active metabolite. An example of a 5-FU derivative is an agent containing tegafur. A 5-FU derivative preferably is a combination drug comprising tegafur. Specific examples include a combination drug comprising tegafur and uracil, a combination drug comprising tegafur, gimeracil, and oteracil potassium, doxifluridine, capecitabine, and carmofur. The combination drug comprising tegafur, gimeracil, and oteracil potassium (e.g., TS-1 (registered trademark), Taiho Phamaceutical Co., Ltd.) described below is particularly preferable.

The agent for potentiating antitumor effects of the 5-FU antitumor agent of the present invention may comprise the RNAi-molecule or the shRNA-molecule-expressing vector of the present invention alone or in combinations of two or more. The agent preferably comprises the shRNA-molecule-expressing vector. The shRNA expression vector preferably expresses the shRNA molecule represented by SEQ ID NO: 8.

The amount of the RNAi-molecule or the shRNA-molecule-expressing vector of the present invention contained in the agent for potentiating antitumor effects of the 5-FU antitumor agent of the present invention can vary depending on factors such as age, body weight, or severity of a patient's disease. A dose can be adequately determined within the range from 0.0001 mg to 100 mg per kg of body weight.

The agent for potentiating antitumor effects of the 5-FU antitumor agent of the present invention can be adequately prepared in accordance with a known technique, depending on factors such as route of administration or target of administration, as with the case of the antitumor agent. The RNAi-molecule or the shRNA-molecule-expressing vector contained in the agent can be delivered to target tissue or cells via a variety of techniques that are commonly employed in the field of gene therapy.

Effects of the agent for potentiating antitumor effects of the 5-FU antitumor agent of the present invention can be evaluated by administering the 5-FU antitumor agent and the agent for potentiating antitumor effects of the 5-FU antitumor agent of the present invention to cells or tissue originating from cancer or to individuals afflicted with cancer, comparing the tumor size thereof with that of the cells, tissue, or an individual to which the 5-FU antitumor agent had been administered alone, and using the results of comparison (i.e., tumor shrinkage or elimination) as an indicator. Cancer cells that can be used for the evaluation of effects of the agent for potentiating antitumor effects of the 5-FU antitumor agent of the present invention are not particularly limited, provided that TS is expressed. Examples thereof include the DLD-1/5FU, KM12C/5FU, and HT29/5FU human colorectal cancer cell lines and the NUGC-3/5FU human gastric cancer cell line. The 5-FU antitumor agent and the agent for potentiating antitumor effects of the 5-FU antitumor agent of the present invention can be administered simultaneously or separately.

With the use of the agent for potentiating antitumor effects of the 5-FU antitumor agent of the present invention in combination with the 5-FU antitumor agent, antitumor effects of 5-FU antitumor agents can be improved by two, three, four, five, ten, twenty, thirty, forty, fifty, or more times.

The agent for potentiating antitumor effects of the 5-FU antitumor agent of the present invention is capable of potentiating antitumor effects of 5-FU antitumor agents. Thus, the dose of the 5-FU antitumor agent required for the treatment of patients afflicted with cancers described above can be reduced. This can suppress or the delay development of side effects that can be caused by administration of the 5-FU antitumor agent. Examples of side effects include, but are not limited to, bone-marrow suppression, hemolytic anemia, disseminated intravascular coagulation syndrome, fulminant hepatic failure, dehydration, enteritis, interstitial pneumonia, stomatitis, gastrointestinal tract ulcer, gastrointestinal hemorrhage, perforation of the digestive tract, acute renal failure, muco-cutaneo-ocular syndrome, toxic epidermal necrolysis, psychoneurotic disorder, acute pancreatitis, rhabdomyolysis, and anosmia.

(c) Pharmaceutical Composition Used for Treatment and/or Prevention of Cancer

The pharmaceutical composition used for treatment and/or prevention of cancer of the present invention comprises, as active ingredients, the RNAi-molecule or the shRNA-molecule-expressing vector of the present invention and the 5-FU antitumor agent. The pharmaceutical composition of the present invention exhibits high TS expression levels and thus can be used for treatment and/or prevention of cancer exhibiting resistance to the 5-FU antitumor agent.

Cancers exhibiting high TS expression levels can be treated with the use of the pharmaceutical composition of the present invention. Examples of such cancers include, but are not particularly limited to, colorectal cancer, liver cancer, kidney cancer, head and neck cancer, esophageal cancer, gastric cancer, biliary tract cancer, gallbladder and bile duct cancer, pancreatic cancer, lung cancer, breast cancer, ovarian cancer, cervical cancer, uterine body cancer, bladder cancer, prostate cancer, testicular tumor, osteogenic and soft-tissue sarcomas, leukaemia, malignant lymphoma, multiple myeloma, skin cancer, and brain tumor. Preferable examples are colorectal cancer, gastric cancer, head and neck cancer, lung cancer, breast cancer, pancreatic cancer, biliary tract cancer, and liver cancer, with colorectal cancer being particularly preferable.

The 5-FU antitumor agent contained in the pharmaceutical composition of the present invention is not limited to 5-FU, and a 5-FU derivative comprising 5-FU as an active metabolite is within the scope of the 5-FU antitumor agent. An example of a 5-FU derivative is an agent containing tegafur. A combination drug comprising tegafur is preferable, and specific examples include a combination drug comprising tegafur and uracil, a combination drug comprising tegafur, gimeracil, and oteracil potassium, doxifluridine, capecitabine, and carmofur. A combination drug comprising tegafur, gimeracil, and oteracil potassium is particularly preferable.

Tegafur is a known compound denoted as 5-fluoro-1-(2-tetrahydrofury;)-2,4-(1H,3H)-pyrimidinedione, it is activated in vivo, and it releases 5-FU, which is an antitumor active substance. Tegafur can be prepared in accordance with a known technique, such as the method disclosed by JP Patent Publication (Kokoku) No. S49-10510 B (1974).

Gimeracil is a known compound denoted as 2,4-dihydroxy-5-chloropyridine, and it does not have any antitumor activity. Gimeracil suppresses inactivation of 5-FU upon metabolism in vivo, and it can potentiate antitumor effects.

Oteracil potassium is a known compound denoted as monopotassium 1,2,3,4-tetrahydro-2,4-dioxo-1,3,5-triazine-6-carboxylate, and it does not have any antitumor activity. Oteracil potassium is mainly distributed in the gastrointestinal tract, and it suppresses 5-FU activation therein to suppress gastrointestinal tract disorders.

Preferable amounts of tegafur, gimeracil, and oteracil potassium incorporated into a combination drug comprising tegafur, gimeracil, and oteracil potassium are not particularly limited, provided that each compound is capable of exerting the effects of interest. Such amounts may be the same as those of the known combination drug disclosed in JP Patent No. 2,614,164. For example, approximately 0.1 to 5 moles, and preferably approximately 0.2 to 1.5 moles of gimeracil, and approximately 0.1 to 5 moles, and preferably approximately 0.2 to 2 moles of oteracil potassium may be incorporated for each mole of tegafur as the amount per day. Particularly preferably, the amounts of active ingredients (i.e., tegafur, gimeracil, and oteracil potassium) incorporated are 1:0.4:1 by mole. A combination drug comprising tegafur, gimeracil, and oteracil potassium comprising tegafur, gimeracil, and oteracil potassium at a ratio of 1:0.4:1 by mole is occasionally referred to as "S-1" herein.

The pharmaceutical composition of the present invention may comprise the RNAi-molecule or the shRNA-molecule-expressing vector of the present invention alone or in combinations of two or more such vectors. The pharmaceutical composition preferably comprises an shRNA-molecule-expressing vector. More preferably, the shRNA-molecule-expressing vector expresses the shRNA molecule represented by SEQ ID NO: 8.

The pharmaceutical composition of the present invention may be a combination drug comprising the RNAi-molecule or the shRNA-molecule-expressing vector and tegafur, gimeracil, and oteracil potassium at an adequate mixing ratio (i.e., a drug comprising a plurality of active ingredients; a single-active ingredient preparation). Alternatively, the pharmaceutical composition may be in the form of a multiple-component drug comprising any of the above active ingredients as a single active component (i.e., a drug comprising a single active ingredient) or a combination drug (i.e., a multiple-component dosage form), so that such active ingredients can be used simultaneously or separately. Tegafur, gimeracil, and oteracil potassium are preferably prepared in the form of combination drugs in a single dosage form, and the RNAi-molecule or the shRNA-molecule-expressing vector is preferably prepared in the form of a single-active-ingredient preparation.

Dosage forms for such drug preparations are not particularly limited and can be adequately selected in accordance with the purpose of treatment. Specific examples include oral preparations (e.g., tablets, coated tablets, powder, granules, capsules, and liquid preparations), injection preparations, suppositories, adhesive skin patches, and ointments. When the pharmaceutical composition of the present invention is present in a multiple-component drug preparation, such drug preparation may have the same or different dosage forms. For example, it is preferable that a combination drug comprising tegafur, gimeracil, and oteracil potassium be in the form of an oral preparation and the RNAi-molecule or the shRNA-molecule-expressing vector be in the form of an injection preparation.

The pharmaceutical composition of the present invention may be prepared, packaged, and distributed separately for each drug preparation, provided that the combination drug comprising tegafur, gimeracil, and oteracil potassium is administered in combination with the RNAi-molecule or the shRNA-molecule-expressing vector. Alternatively, all or some of the drug preparations may be prepared, packaged, and distributed in a single-package form suitable for administration of such drugs in combination (i.e., a kit formulation).

Drug preparations comprising active ingredients of the pharmaceutical composition of the present invention can be prepared in accordance with a known technique with the use of pharmacologically acceptable carriers. Examples of such carriers include various substances that are generally used for drug preparations, such as excipients, binders, disintegrators, lubricants, diluents, solubilizers, suspending agents, isotonizing agents, pH modifiers, buffers, stabilizers, colorants, flavoring agents, and corrigents.

Examples of excipients include lactose, sucrose, sodium chloride, glucose, maltose, mannitol, erythritol, xylitol, maltitol, inositol, dextran, sorbitol, albumin, urea, starch, calcium carbonate, kaoline, crystalline cellulose, silica, methylcellulose, glycerine, sodium alginate, gum Arabic, and a mixture of any thereof. Examples of lubricants include purified talc, stearate, sodium borate, polyethylene glycol, and a mixture of any thereof. Examples of binders include simple syrup, glucose solution, starch solution, gelatin solution, polyvinyl alcohol, polyvinyl ether, polyvinyl pyrrolidone, carboxymethyl cellulose, shellac, methylcellulose, ethyl cellulose, water, ethanol, potassium phosphate, and a mixture of any thereof. Examples of disintegrators include dry starch, sodium alginate, agar powder, laminaran powder, sodium bicarbonate, calcium carbonate, polyoxyethylene sorbitan fatty acid esters, sodium lauryl sulfate, stearic acid monoglyceride, starch, lactose, and a mixture of any thereof. Examples of diluents include water, ethyl alcohol, macrogol, propylene glycol, ethoxylated isostearyl alcohol, polyoxylated isostearyl alcohol, polyoxyethylene sorbitan fatty acid esters, and a mixture of any thereof. Examples of stabilizers include sodium pyrosulfife, ethylenediaminetetraacetic acid, thioglycolic acid, thiolactic acid, and a mixture of any thereof Examples of isotonizing agents include sodium chloride, boric acid, glucose, glycerine, and a mixture of any thereof. Examples of pH modifiers and buffers include sodium citrate, citric acid, sodium acetate, sodium phosphate, and a mixture of any thereof. Examples of soothing agents include procaine hydrochloride, lidocaine hydrochloride, and a mixture of any thereof.

The amounts of active ingredients in the pharmaceutical composition of the present invention to be administered are not particularly limited, provided that such active ingredients are capable of exerting the effects of interest. Such amounts are adequately determined in accordance with age, cancer type, stage, occurrence of metastasis, history of treatment, use of other antitumor agents, and other conditions of the patient. For example, the amount of tegafur is 0.2 to 40 mg/kg/day and preferably 0.5 to 20 mg/kg/day, the amount of gimeracil is 0.05 to 12 mg/kg/day and preferably 0.1 to 6 mg/kg/day, the amount of oteracil potassium is 0.2 to 40 mg/kg/day and preferably 0.5 to 20 mg/kg/day, and the amount of the RNAi-molecule or the shRNA-molecule-expressing vector is 0.0001 to 100 mg/kg/day.

The order and intervals of administration of active ingredients of the pharmaceutical composition of the present invention are not particularly limited, provided that synergistic effects resulting from the use of such active ingredients in combination can be attained. When the pharmaceutical composition of the present invention is prepared in the form of a kit, the drugs may be administered simultaneously or separately.

Effects of the pharmaceutical composition of the present invention can be evaluated by administering the pharmaceutical composition to a cell or tissue originating from the above-mentioned cancer or to an individual afflicted with such cancer, comparing the tumor size thereof with that in the cell or tissue or with an individual to which the pharmaceutical composition has not been administered (or not yet been administered), and using the results of comparison (i.e., tumor shrinkage or elimination) as an indicator. Cancer cells that can be used for the evaluation of effects of the pharmaceutical composition of the present invention are not particularly limited, provided that TS is expressed. Examples thereof include the DLD-1/5FU, KM12C/5FU, and HT29/5FU human colorectal cancer cell lines and the NUGC-3/5FU human gastric cancer cell line.

The antitumor effects of the pharmaceutical composition of the present invention are not additive effects resulting from antitumor effects of each active ingredient. The antitumor effects of the pharmaceutical composition of the present invention can be synergistic effects resulting from the effects of the 5-FU antitumor agent for potentiating activity exerted by the RNAi-molecule or the shRNA-molecule-expressing vector. The "additive effects" constitute the sum of antitumor effects exerted by each active ingredient, and the additive effects can be represented as values determined by multiplication of tumor growth inhibition rates exerted by active ingredients as described in detail in the examples below. The term "synergistic effects" refers to antitumor effects that are statistically significantly higher than additive antitumor effects exerted by the active ingredients. Such tumor growth inhibition rates are statistically significantly higher than the tumor growth inhibition rate attained by the additive effects brought by active ingredients as described in greater detail in the examples below.

The present invention also relates to a method of cancer treatment involving the use of the antitumor agent, the agent for potentiating antitumor effects of the 5-FU antitumor agent, and/or the pharmaceutical composition of the present invention. Examples of cancers that can be treated by such method include cancers described above.

EXAMPLES

Hereafter, the present invention is described in greater detail with reference to the examples below. However, it should be noted that the present invention is not limited to these examples.

Example 1

Identification of siRNA Molecules Targeting TS

The DLD-1/5FU human colorectal cancer cell lines (Int. J. Oncol., 2000; 17: 277-83) that had been resreported to be resistant to 5-FU were cultured in a 6-cm culture dish for 24 hours until the cells reached 50% to 60% confluence.

Subsequently, siRNA molecules (i.e., TS-siRNA1 molecules (sense strand: SEQ ID NO: 1; antisense strand: SEQ ID NO: 2), TS-siRNA2 molecules (sense strand: SEQ ID NO: 3; antisense strand: SEQ ID NO: 4), and TS-siRNA3 molecules (sense strand: SEQ ID NO: 5; antisense strand: SEQ ID NO: 6)) were chemically synthesized, and 2.5 ml of a solution containing each of the above siRNA molecules (final concentration: 25 nM) and 25 μl of TransIT-TKO Transfection Reagent (Minis) was transfected into the above cells in accordance with a conventional technique. Scrambled siRNA (TS-Scra1) was used as a negative control.

The effects of siRNA molecules on inhibition of TS expression were inspected via Taqman real-time PCR (ABI PRISM 7700 Sequence Detection System; Applied Biosystems) 72 hours after transfection. The Assays-on-Demand Gene Expression Assay Mix (assay ID Hs00426591_ml; PCR product size: 87 bp; Applied Biosystems) was used for TS primers and probes. GAPDH was used as the internal standard (Assays-on-Demand Gene Expression System; assay ID: Hs99999905_ml; PCR product size: 122 bp; Applied Biosystems).

The results are shown in FIG. 1. TS-siRNA1 to TS-siRNA3 exhibited effects of inhibiting TS expression, and the effects of TS-siRNA1 on inhibition of TS expression were stronger than those of TS-siRNA2 and TS-siRNA3 (83.5±1.3%).

Example 2

Construction of Adenovirus Vector Expressing shRNA Molecule Targeting TS

Template DNA of the shRNA molecule targeting TS was synthesized based on TS-siRNA1 (TS-siRNA1 sense strand (GTAACACCATCGATCATGA, SEQ ID NO: 9), linker region (TAGTGCTCCTGGTTG, SEQ ID NO: 10), TS-siRNA1 antisense strand (TCATGATCGATGGTGT-TAC, SEQ ID NO: 11), and polymerase III terminator (TTTTTT)). In order to prepare a plasmid vector expressing the shRNA molecule targeting TS, the resulting template was inserted into the pBAsi-hU6 plasmid vector (Takara Bio Inc.) containing a human U6 promoter.

Subsequently, the human U6 promoter cleaved from the plasmid vector with EcoRV and the template were inserted into the pAxcwit cosmid vector using the Adenovirus Expression Vector kit (Takara Bio Inc.). An E1-deficient adenovirus vector expressing the shRNA molecule targeting TS (hereafter, referred to as "Ad-shTS") was constructed by the COS-TPC method (Jpn. J. Med. Sci. Biol., 1994; 47: 157-66). An adenovirus vector containing the bacterial LacZ gene (hereafter, referred to as "Ad-LacZ") was used as a control (Oncogene, 2004, 23: 7475-83).

Example 3

Action of Potentiating Antitumor Effects of TS-Targeted shRNA Molecule on TS-1

Subcutaneously subcultured fragments of DLD-1/5FU human colorectal cancer cell lines each having a volume of approximately 8 mm³ were transplanted into the backs of 6-week-old male nude mice, and the mice were divided into groups each consisting of 6 individuals when the tumor volume became approximately 200 mm³. Ad-shTS (2×10⁹ pfu) was injected into the tumor every 4 days over the period of 16 days in the group to which Ad-shTS had been administered (hereafter, referred to as the "Ad-shTS group") and in the group to which Ad-shTS and S-1 had been administered (hereafter, referred to as the "Ad-shTS+S-1 group"). To the Ad-shTS+S-1 group and the group to which S-1 had been administered (hereafter, referred to as the "S-1 group"), 10 mg/kg of S-1 (Taiho Phamaceutical Co., Ltd.) was orally administered once a day for 14 continuous days. The initial Ad-shTS administration was carried out 2 days before the initiation of S-1 administration. Regarding the control group, PBS was injected into the tumor every 4 days over a period of 16 days.

Thereafter, the tumor size was measured every 3 days over a period of 30 days, and tumor growth in each mouse was inspected. The tumor volume and the tumor growth rate were determined using the equations below.

Tumor volume (mm³)=(long diameter of tumor)× (short diameter of tumor)²×0.5

Tumor growth rate=(tumor volume on the day of measurement)/(tumor volume at the initiation of administration)

Figure 2:
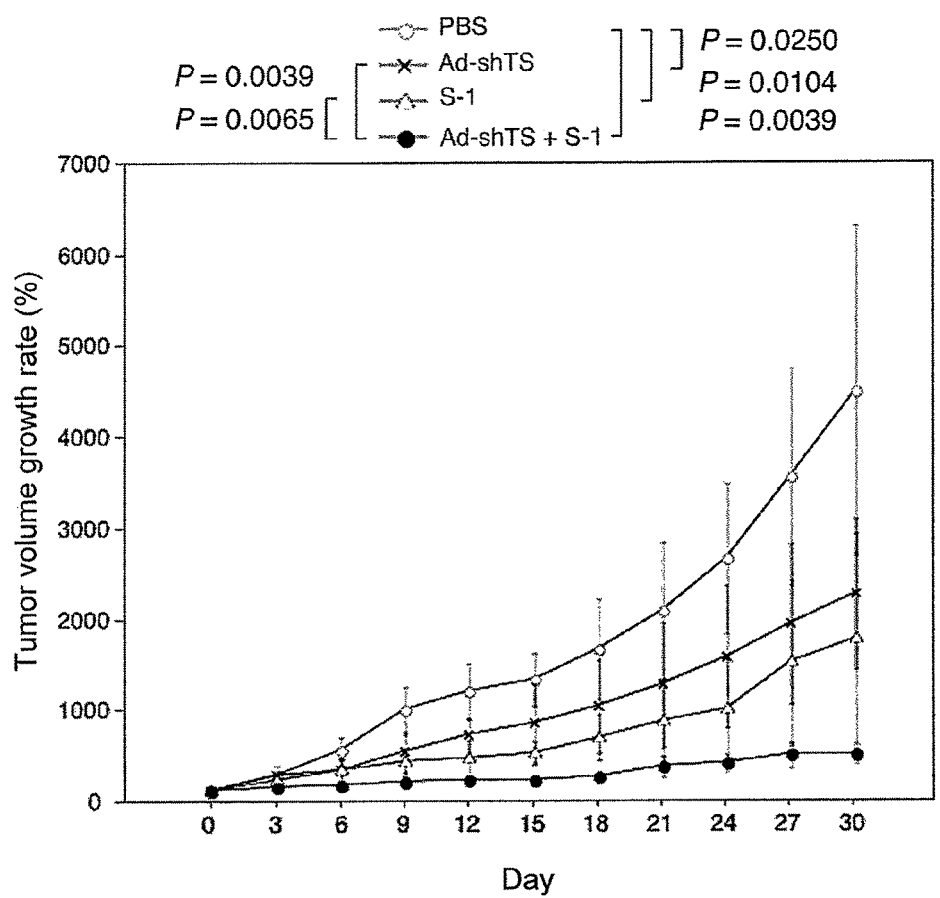
FIG. 2 is a characteristic diagram showing antitumor effects of TS-targeted shRNA and/or S-1 in mice carrying DLD-1/5FU human colorectal cancer cell lines.

The results are shown in FIG. 2. While the tumor growth rate of the control group was 44.5±18.0 on day 30, that of the Ad-shTS group was 22.3±8.2, that of the S-1 group was 17.4±11.5, and that of the Ad-shTS+S-1 group was 4.7±0.9. Thus, antitumor effects of the Ad-shTS+S-1 group were found to be statistically significantly higher than those of the control group, the Ad-shTS group, and the S-1 group.

The tumor growth inhibitory ratio (%) of the Ad-shTS group was 50% and that of the S-1 group was 39% relative to the control group (i.e., the tumor growth rate of a group to which each agent had been administered on day 30/tumor growth rate of the control group on day 30×100). When the action potentiating the antitumor effects attained by the use of Ad-shTS in combination with S-1 results in additive effects, the tumor growth inhibitory rate of the Ad-shTS+S-1 group relative to the control group is considered to be 20%, which is determined by multiplying the tumor growth inhibitory ratio of the Ad-shTS group by that of the S-1 group (i.e., 50%× 39%=20%). However, the actually determined value was 11%. This indicates that the actions of potentiating antitumor effects attained by the use of Ad-shTS in combination with S-1 are synergistic effects.

Industrial Applicability

The RNAi molecule targeting TS mRNA according to the present invention is capable of inhibiting the TS expression level in tumor cells and is also capable of inhibiting tumor cell growth. By suppressing the TS expression level with the use of the RNAi molecule of the present invention, antitumor effects of 5-FU antitumor agents can be potentiated and cancer can be treated and/or prevented effectively.

All publications, patents, and patent applications cited herein are incorporated herein by reference in their entirety.

The invention claimed is:

1. An RNAi molecule capable of suppressing expression of thymidylate synthase by RNAi action comprising a double-stranded RNA domain, which consists of the nucleotide sequence represented by SEQ ID NO: 8.

2. A vector comprising template DNA of an RNAi molecule which consists of the nucleotide sequence represented by SEQ ID NO: 8 and which expresses the RNAi molecule.

3. An antitumor agent comprising the RNAi molecule according to claim 1.

4. A pharmaceutical composition used for treatment and/or prevention of cancer comprising the RNAi molecule according to claim 1 in combination with a 5-FU antitumor agent.

5. The pharmaceutical composition according to claim 4, wherein the 5-FU antitumor agent is a combination drug comprising tegafur.

6. The pharmaceutical composition according to claim 5, wherein the 5-FU antitumor agent is a combination drug comprising tegafur, gimeracil, and oteracil potassium.

7. The pharmaceutical composition according to claim 6, which comprises tegafur, gimeracil, and oteracil potassium at a ratio of 1:0.4:1 by mole.

8. The pharmaceutical composition according to claim 4, wherein the RNAi molecule, and the 5-FU antitumor agent are each a single-active-ingredient preparation.

9. The pharmaceutical composition according to claim 4, wherein the RNAi molecule and the 5-FU antitumor agent are in the form of a kit formulation.

10. An agent for potentiating antitumor effects of a 5-FU antitumor agent comprising the RNAi molecule according to claim 1.

11. The agent for potentiating antitumor effects according to claim 10, wherein the 5-FU antitumor agent is a combination drug comprising tegafur.

12. The agent for potentiating antitumor effects according to claim 11, wherein the 5-FU antitumor agent is a combination drug comprising tegafur, gimeracil, and oteracil potassium.

13. An antitumor agent comprising the vector according to claim 2.

14. A pharmaceutical composition used for treatment and/or prevention of cancer comprising the vector of claim 2 in combination with a 5-FU antitumor agent.

15. An agent for potentiating antitumor effects of a 5-FU antitumor agent comprising the vector according to claim 2.

* * * * *

SEQUENCE LISTING

<160> NUMBER OF SEQ ID NOS: 11

<210> SEQ ID NO 1
<211> LENGTH: 19
<212> TYPE: RNA
<213> ORGANISM: Artificial
<220> FEATURE:

<223> OTHER INFORMATION: synthetic oligonucleotide

<400> SEQUENCE: 1
guaacaccau cgaucauga                                                    19

<210> SEQ ID NO 2
<211> LENGTH: 19
<212> TYPE: RNA
<213> ORGANISM: Artificial
<220> FEATURE:
<223> OTHER INFORMATION: synthetic oligonucleotide

<400> SEQUENCE: 2
ucaugaucga ugguguuac                                                    19

<210> SEQ ID NO 3
<211> LENGTH: 19
<212> TYPE: RNA
<213> ORGANISM: Artificial
<220> FEATURE:
<223> OTHER INFORMATION: synthetic oligonucleotide

<400> SEQUENCE: 3
gaauacagag auauggaau                                                    19

<210> SEQ ID NO 4
<211> LENGTH: 19
<212> TYPE: RNA
<213> ORGANISM: Artificial
<220> FEATURE:
<223> OTHER INFORMATION: synthetic oligonucleotide

<400> SEQUENCE: 4
auuccauauc ucuguauuc                                                    19

<210> SEQ ID NO 5
<211> LENGTH: 19
<212> TYPE: RNA
<213> ORGANISM: Artificial
<220> FEATURE:
<223> OTHER INFORMATION: synthetic oligonucleotide

<400> SEQUENCE: 5
cgaucaugau guagagugu                                                    19

<210> SEQ ID NO 6
<211> LENGTH: 19
<212> TYPE: RNA
<213> ORGANISM: Artificial
<220> FEATURE:
<223> OTHER INFORMATION: synthetic oligonucleotide

<400> SEQUENCE: 6
acacucuaca ucaugaucg                                                    19

<210> SEQ ID NO 7
<211> LENGTH: 15
<212> TYPE: RNA
<213> ORGANISM: Artificial
<220> FEATURE:
<223> OTHER INFORMATION: synthetic oligonucleotide

<400> SEQUENCE: 7
uagugcuccu gguug                                                        15

<210> SEQ ID NO 8

```
<211> LENGTH: 53
<212> TYPE: RNA
<213> ORGANISM: Artificial
<220> FEATURE:
<223> OTHER INFORMATION: synthetic oligonucleotide

<400> SEQUENCE: 8
guaacaccau cgaucaugau agugcuccug guugucauga ucgauggugu uac          53

<210> SEQ ID NO 9
<211> LENGTH: 19
<212> TYPE: DNA
<213> ORGANISM: Artificial
<220> FEATURE:
<223> OTHER INFORMATION: synthetic oligonucleotide

<400> SEQUENCE: 9
gtaacaccat cgatcatga                                                19

<210> SEQ ID NO 10
<211> LENGTH: 15
<212> TYPE: DNA
<213> ORGANISM: Artificial
<220> FEATURE:
<223> OTHER INFORMATION: synthetic oligonucleotide

<400> SEQUENCE: 10
tagtgctcct ggttg                                                    15

<210> SEQ ID NO 11
<211> LENGTH: 19
<212> TYPE: DNA
<213> ORGANISM: Artificial
<220> FEATURE:
<223> OTHER INFORMATION: synthetic oligonucleotide

<400> SEQUENCE: 11
tcatgatcga tggtgttac                                                19
```